United States Patent [19]
Brown et al.

[11] Patent Number: 5,683,424
[45] Date of Patent: *Nov. 4, 1997

[54] NON-INVASIVE MONITORING AND TREATMENT OF SUBJECTS IN CARDIAC ARREST USING ECG PARAMETERS PREDICTIVE OF OUTCOME

[75] Inventors: Charles G. Brown; Roger R. Dzwonczyk, both of Columbus, Ohio

[73] Assignee: The Ohio State University Research Foundation, Columbus, Ohio

[*] Notice: The term of this patent shall not extend beyond the expiration date of Pat. No. 5,571,142.

[21] Appl. No.: 663,482

[22] Filed: Jun. 13, 1996

Related U.S. Application Data

[63] Continuation of Ser. No. 298,376, Aug. 30, 1994, Pat. No. 5,571,142.
[51] Int. Cl.$^6$ .............................. A61N 1/39; A61B 5/046
[52] U.S. Cl. .................. 607/5; 128/705; 128/200.24; 604/890.1
[58] Field of Search ...................... 607/5, 7; 128/696, 128/697, 702, 704, 705, 708, 200.24; 364/413.05, 413.06; 604/890.1, 891.1

[56] References Cited

U.S. PATENT DOCUMENTS

| | | |
|---|---|---|
| 4,296,755 | 10/1981 | Judell . |
| 4,680,708 | 7/1987 | Ambos et al. . |
| 4,924,875 | 5/1990 | Chamoun . |
| 4,928,674 | 5/1990 | Halperin et al. . |
| 4,974,162 | 11/1990 | Siegel et al. . |
| 5,077,667 | 12/1991 | Brown et al. . |
| 5,092,341 | 3/1992 | Kelen . |
| 5,423,325 | 6/1995 | Burton . |
| 5,423,863 | 6/1995 | Felblinger et al. . |
| 5,437,285 | 8/1995 | Verrier et al. . |

OTHER PUBLICATIONS

Brown, Charles G., M.D. et al., "Physiologic Measurement of the Ventricular Fibrillation of ECG Signal: Estimating the Duration of Ventricular Fibrillation," *Annals of Emergency Medicine*, 22:1, Jan., 1993, pp. 70–74.

Brown, Charles G., M.D. et al., "Non–Invasive Monitoring During Ventricular Fibrillation," *Applied Cardiopulmonary Pathophysiology*, vol. 4, 1992, pp. 293–299.

Brown, Charles G., M.D. et al., "Median Frequency—A New Parameter for Predicting Defibrillation Success Rate," *Annals of Emergency Medicine*, 20:7, Jul., 1991, pp. 787–789.

Martin, Daniel R. et al., "Frequency Analysis of the Human and Swine Electrocardiogram During Ventricular Fibrillation," *Resuscitation*, vol. 22, 1991, pp. 85–91.

Dzwonczyk, Roger et al., "The Median Frequency of the ECG During Ventricular Fibrillation: Its Use in an Algorithm for Estimating the Duration of Cardiac Arrest," *IEEE Transactions of Biomedical Engineering*, vol. 37, No. 6, Jun., 1990, pp. 640–645.

Brown, Charles G., M.D., F.A.C.E.P. et al., "Estimating the Duration of Ventricular Fibrillation," *Annals of Emergency Medicine*, 18:11, Nov., 1989, pp. 1181–1185.

(List continued on next page.)

*Primary Examiner*—Jeffrey R. Jastrzab
*Attorney, Agent, or Firm*—Van Dyke, Gardner, Linn & Burkhart, LLP

[57] ABSTRACT

A method and apparatus for determining the metabolic state of the myocardium of a subject in ventricular fibrillation or asystole and/or for guiding therapeutic interventions. Electrocardiogram signals of the subject's heart are transformed to a frequency domain power spectrum, and at least one frequency parameter is monitored and processed to a value predictive of a clinically relevant cardiac arrest outcome. In the preferred embodiment, centroid frequency and/or peak power frequency of the power spectrum are monitored.

32 Claims, 13 Drawing Sheets

OTHER PUBLICATIONS

Dzwonczyk, Roger, PE et al., "Frequency Analysis of the Human ECG During Ventricular Fibrillation" *IEEE*, 1989, pp. 3, 4.

Dzwonczyk, Roger et al., "Frequency Analysis of the ECG During Ventricular Fibrillation," *IEEE/Ninth Annual Conference of the Engineering in Medicine and Biology Society*, 1987, pp. 0147–0148.

Brown, Charles G. et al., "Frequency Analysis of the Electrocardiogram in Human Beings During Ventricular Fibrillation," *Annals of Emergency Medicine*, 18:4, Apr., 1989, p. 440 (abstract).

Menegazzi J.J., Watanabe S., Klain M., Doctor A., "ECG Spectrum Analysis Predicts Return of Spontaneous Circulation Following Prolonged Ventricular Fibrillation," *NAEMSP Abstracts*, Jul.–Sep., 1993, p. S61.

Forster, F.K. et al., "Recognition of Ventricular Fibrillation, Other Rhythms and Noise in Patients Developing the Sudden Cardiac Death Syndrome," *Conference: Computers in Cardiology, Ninth Meeting of Computers in Cardiology*, 1982, pp. 245–248 (abstract only).

Nolle, F.M. et al., "Power Spectrum Analysis of Ventricular Fibrillation and Imitative Artifacts," *Conference: Computers in Cardiology*, 1981, pp. 209–212 (abstract only).

Herbschleb, J.N. et al., "Frequency Analysis of the ECG Before and During Ventricular Fibrillation," *Conference: Computers in Cardiology*, 1980, pp. 365–368 (abstract only).

Nygards, Mats–Erick et al., "Recognition of Ventricular Fibrillation Utilizing the Power Spectrum of the ECG," *Conference: Computers in Cardiology*, Oct., 1977, pp. 393–397 (abstract only).

Yakaitis, Ronald W., M.D. et al., "Influence of Time and Therapy on Ventricular Defibrillation in Dogs," *Critical Care Medicine*, vol. 8, No. 3, Mar., 1989, pp. 157–163.

Niemann, James T., M.D. et al., "Treatment of Prolonged Ventricular Fibrillation Immediate Countershock Versus High–Dose Epinephrine and CPR Preceding Countershock," *Circulation*, vol. 85, No. 1, Jan., 1992, pp. 281–287.

Ditchey, Roy V., M.D. et al., "Failure of Epinephrine to Improve the Balance Between Myocardial Oxygen Supply and Demand During Closed–Chest Resuscitation in Dogs," *Circulation*, vol. 78, No. 2, Aug., 1988, pp. 382–389.

Niemann, James T., M.D. et al., "Endocardial and Transcutaneous Cardiac Pacing, Calcium Chloride, and Epinephrine in Postcountershock Asystole and Bradycardias," *Critical Care Medicine*, vol. 13, No. 9, Sep., 1985, pp. 699–704.

Gaba, David M. et al., "Myocardial Damage Following Transthoracic Direct Current Countershock in Newborn Piglets," *Pediatric Cardiology*, vol. 2, 1982, pp. 281–288.

Hargarten, Kathleen M., M.D., F.A.C.E.P. et al., "Prehospital Experience With Defibrillation of Coarse Ventricular Fibrillation: A Ten–Year Review", *Annals of Emergency Medicine*, 19:2, Feb., 1990, pp. 157–162.

Martin, G. et al., "Relation Between Power Spectrum Time Course During Ventricular Fibrillation and Electromechanical Dissociation. Effects of Coronary Perfusion and Nifedipine," *European Heart Journal*, vol. 7, 1986, pp. 560–569.

Martin, G. et al., "Effects of Calcium Antagonists on Time Course of ECG Power Spectrum During Ventricular Fibrillation," *Computers in Cardiology*, IEEE Computer Society, 1983, pp. 213–216.

Martin, G. et al., "Differences in the Time Course of the Power Spectrum During Ventricular Fibrillation," *The Applications of Computers in Cardiology: State of the Art & New Perspectives*, 1984, pp. 179–183.

Kuo, S., S.M. et al., "Computer Detection of Ventricular Fibrillation," *Conference: Computers in Cardiology*, Sep., 1978, pp. 347, 348 (abstract only).

NON-INVASIVE MONITORING AND TREATMENT OF SUBJECTS IN CARDIAC ARREST USING ECG PARAMETERS PREDICTIVE OF OUTCOME

This is a continuation of application Ser. No. 08/298,376, filed Aug. 30, 1994 now U.S. Pat. No. 5,571,142.

BACKGROUND OF THE INVENTION

This invention relates generally to the monitoring and treatment of a human or animal subject in cardiac arrest from the electrocardiogram (ECG) of the subject's heart. More particularly, the invention is related to determining clinically useful parameters from the subject's ECG which help guide therapeutic interventions during ventricular fibrillation. As used herein, ventricular fibrillation is intended to include asystole which may be considered a form of ventricular fibrillation.

Each year more than 350,000 sudden cardiac deaths occur in the United States. The successful development and implementation of emergency medical services has resulted in saving many of these subjects. Training the public to perform basic lifesaving maneuvers, like cardiopulmonary resuscitation (CPR), as well as providing easy and early access to medical help, which provides skilled rescuers at the subject's location within minutes of the arrest, has saved lives. However, survival from out-of-hospital cardiac arrest is much lower than theoretically possible. Even the advent of automatic and semi-automatic external defibrillators, and their widespread use by first responders to victims of sudden cardiac death, has had only a modest impact on survival.

Although electrical countershock is the most effective treatment of ventricular fibrillation, there is biochemical, histological, and clinical evidence to suggest that electrical countershock can cause myocardial injury. When the duration of ventricular fibrillation is prolonged and the heart is not metabolically conducive to countershock administration, the cumulative energy applied from unsuccessful countershocks to the fibrillating myocardium may impair subsequent efforts at successfully converting the heart to a pulsatile rhythm, that is a cardiac rhythm that allows effective perfusion to the subject. Thus, after more prolonged durations of ventricular fibrillation, therapy aimed at improving myocardial perfusion and, thus, the metabolic state of the myocardium, prior to countershock administration, appears to optimize outcome.

In our U.S. Pat. No. 5,077,667 entitled MEASUREMENT OF THE APPROXIMATE ELAPSED TIME OF VENTRICULAR FIBRILLATION AND MONITORING THE RESPONSE OF THE HEART TO THERAPY, we disclosed a technique for accurately estimating the elapsed time of a subject in ventricular fibrillation. In our patent, time domain samples of the subject's electrocardiogram (ECG) signal are transformed to a frequency domain spectrum and the median frequency, which bisects the energy of the power spectrum, is detected. The median frequency is compared with a pattern of experimentally obtained median frequency data to estimate the elapsed time of ventricular fibrillation. This information may be used to establish the most appropriate time to countershock a subject.

Estimation of the elapsed time of ventricular fibrillation can be affected by many factors. These include whether the subject received cardiopulmonary resuscitation prior to the time that the measurement was made and the degree of perfusion of the heart. For example, the subject may be in cardiac arrest clinically but still have some degree of myocardial perfusion when the heart is in a rhythm called "ventricular tachycardia" or "Torsades de Pointes". Thus, when cardiopulmonary resuscitation generates adequate myocardial perfusion, or if the subject is in a condition with some degree of myocardial perfusion, the metabolic state of the myocardium may not deteriorate as rapidly, despite the fact that the subject is in cardiac arrest clinically. Accordingly, it is desirable to provide a more accurate determination of the metabolic state of the myocardium which takes into account the level of myocardial perfusion prior to measurement of the metabolic state of the myocardium. It is additionally desirable to more accurately predict whether attempts to countershock the subject will result in conversion of the heart to an organized, pulsatile rhythm, in order to avoid the application of unnecessary and potentially harmful countershocks. It is additionally desirable to provide a non-invasive method of guiding therapeutic interventions during ventricular fibrillation and asystole.

SUMMARY OF THE INVENTION

According to one aspect, the invention provides a non-invasive method of guiding therapeutic interventions to a subject in cardiac arrest. The method includes connecting electrodes to the body of the subject and detecting from the electrodes an analog electrical potential which is proportional to the electrical potential generated by the subject's heart. The analog potential is sampled for a selected interval of time to obtain a set of time domain samples. A power distribution of the electrical potential is detected by transforming the time domain samples to a frequency domain power spectrum. At least one amplitude parameter of the ECG time-domain signal interval or frequency parameter of the power spectrum is determined and monitored. The parameter or parameters are predictive of a clinically relevant cardiac arrest outcome for the subject. Therapy is administered to the subject as a function of the value of the parameter or parameters.

According to a more detailed aspect of the invention, one of the parameters that is predictive of clinically relevant cardiac arrest outcome for the subject is the centroid frequency ($F_c$) of the power spectrum. According to another more detailed aspect of the invention, another of the parameters that is predictive of clinically relevant cardiac arrest outcome for the subject is the peak power frequency ($F_p$) of the power spectrum. In a most preferred form, the combined values of the centroid frequency and the peak power frequency are used as predictive of such cardiac arrest outcomes.

According to another aspect of the invention, a non-invasive method of determining myocardial perfusion and, thus, the metabolic state of the myocardium of a subject in ventricular fibrillation or asystole includes connecting electrodes to the body of the subject and detecting from the electrodes an analog electrical potential which is proportional to the electrical potential generated by the subject's heart. The analog potential is sampled for a selected interval of time to obtain a set of time domain samples and the power distribution of the electrical potential is detected by transforming the time domain samples to a frequency domain power spectrum. At least one amplitude parameter of the ECG time-domain signal interval or frequency parameter of the power spectrum is determined and monitored. The parameter or parameters are predictive of a clinically relevant cardiac arrest outcome for the subject. The parameter or parameters are resolved to an indication of the metabolic state of the myocardium of the subject's heart. Preferably, the predictive parameter is selected from a group of parameters including centroid frequency of the power spectrum ($F_c$) and peak power frequency of the power spectrum ($F_p$). The method according to this aspect of the invention may further include applying therapy to a subject in ventricular fibrillation or asystole, assessing the effect of the therapy on the subject utilizing the determined parameter from the subject's ECG, and guiding further therapy based upon the assessment. The method may further include prescribing a particular therapeutic protocol as a function of centroid frequency and/or peak power frequency of the power spectrum.

Other aspects of the invention are embodied in an apparatus that non-invasively establishes a clinically useful characteristic of the heart of a subject in ventricular fibrillation or asystole from an electrocardiogram of the heart. The apparatus includes an analyzer for determining at least one amplitude parameter of the ECG time-domain signal interval or frequency parameter of the power spectrum of the ECG with the parameter being predictive of a clinically relevant cardiac arrest outcome for the subject and the metabolic state of the myocardium. A processor is provided for resolving the parameter or parameters to a clinically useful characteristic of the subject's heart. The apparatus may be used as a monitor alone or in combination with a defibrillator for administering countershocks or other resuscitators in response to a value of the parameter or combination of parameters.

These and other objects, advantages, and features of this invention will become apparent upon review of the following specification in conjunction with the drawings.

DESCRIPTION OF THE PREFERRED EMBODIMENT

Figure 1:
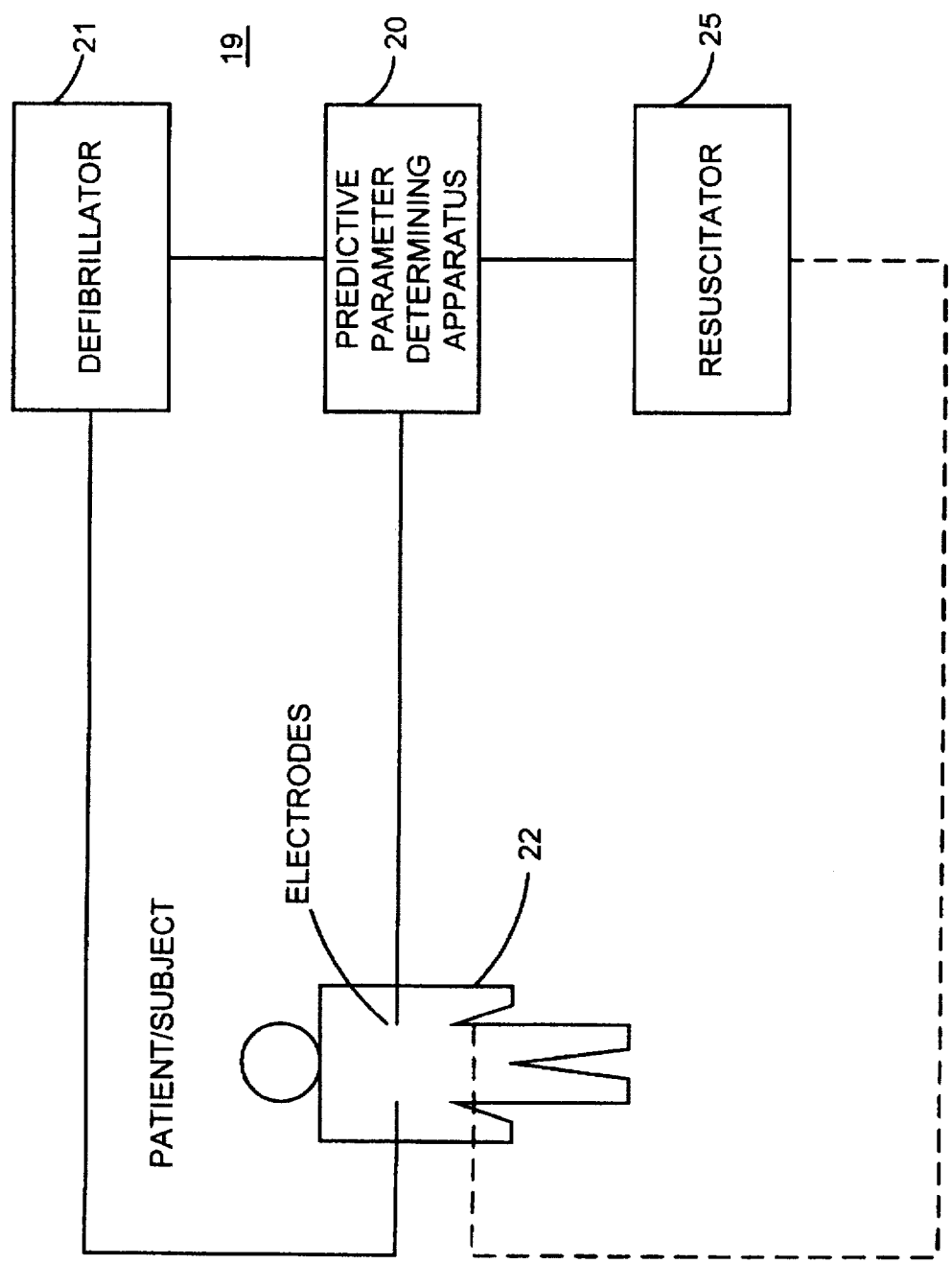
FIG. 1 is a block diagram of an apparatus according to the invention connected with a subject.
Figure 2:
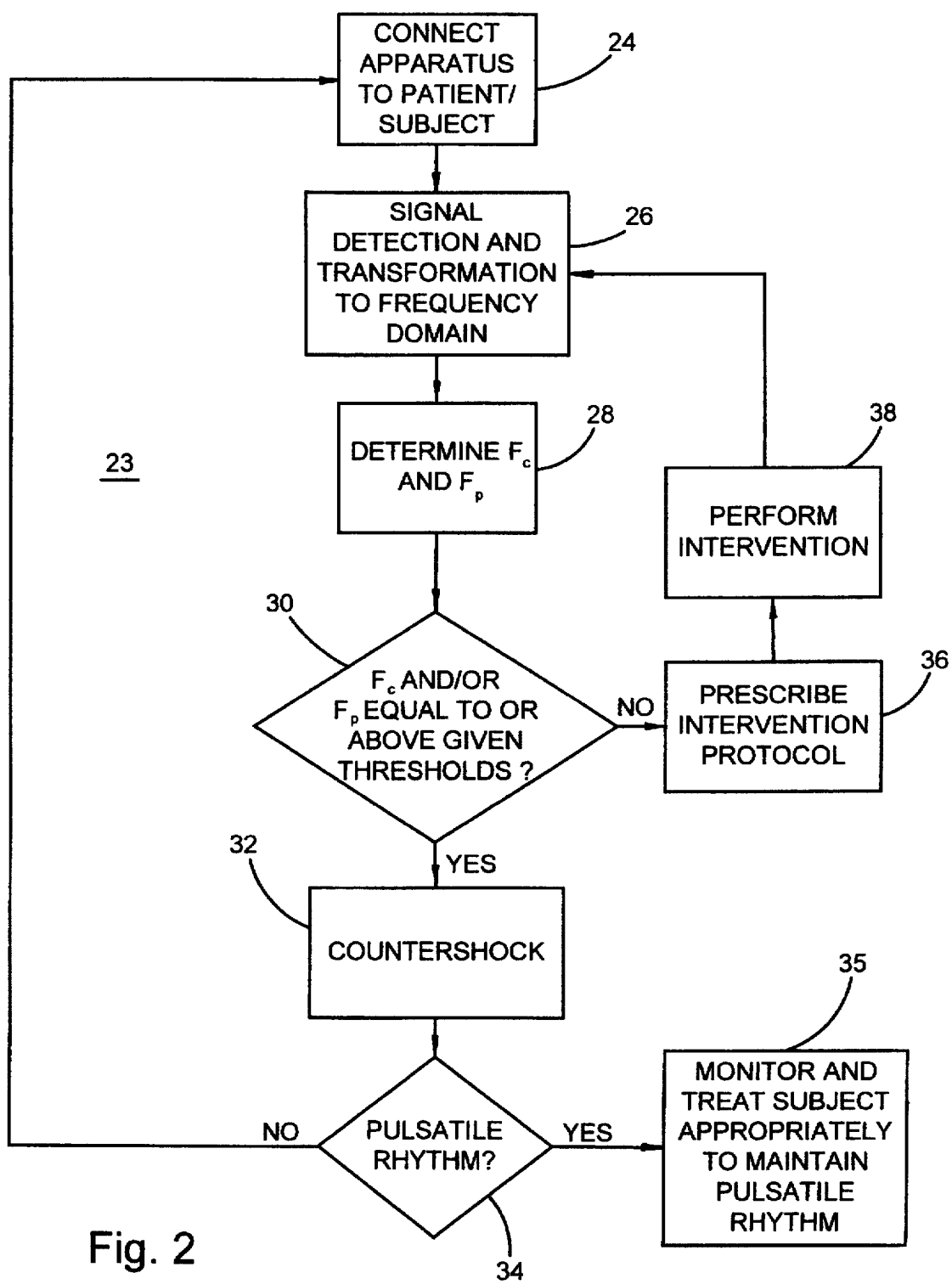
FIG. 2 is a flowchart of a method of treating a subject in ventricular fibrillation, according to the invention.

Referring specifically to the drawings, and the illustrative embodiments depicted therein, an apparatus 19, including a predictive parameter determining apparatus 20 and/or a defibrillator 21, and/or a resuscitator 25, is connected to a subject 22, who is assessed to be in cardiac arrest, utilizing conventional internal or external electrodes (FIG. 1). After the apparatus is connected to the subject at 24, a method 23 of treating the subject with apparatus 19 is performed (FIG. 2). Method 23 includes detecting an analog electrical potential which is proportional to the electrical potential generated by the subject's heart and transforming the analog signal into the frequency domain utilizing a fast Fourier transform algorithm, at 26. The technique for converting the analog signal into the frequency domain is disclosed in U.S. Pat. No. 5,077,667 issued to Charles G. Brown and Roger Dzwonczyk, the disclosure of which is hereby incorporated herein by reference and will not be repeated. The centroid frequency ($F_c$) and the peak power frequency ($F_p$) of the power spectrum are determined at 28. The centroid frequency is defined as the X-axis (frequency) coordinate of the center of spectral mass and it is determined by:

$$F_c = \frac{\sum_{i=1}^{n} (f_i \cdot p_i)}{\sum_{i=1}^{n} p_i}$$

Where $f_i$ equals the ith frequency component and $P_i$ equals the power at $f_i$. Peak power frequency ($F_p$) is the frequency that has the peak power in the power spectrum. The parameters, $F_c$ and $F_p$, are reported in Hertz and provide an estimate of the frequency distribution of the power of a signal in the spectrum.

After $F_c$ and $F_p$ are determined by predictive parameter determining apparatus 20, it is then determined at 30 whether $F_c$ and/or $F_p$ are equal to or above particular thresholds. In the illustrated embodiment, the threshold for $F_p$ may be set in the range between approximately 3.5 Hz and approximately 7.75 Hz and the threshold for $F_c$ may be set in the range between approximately 3.86 Hz and approximately 6.12 Hz. These threshold values are applicable to human subjects and may be different for other species. If $F_c$ and/or $F_p$ are equal to or above their respective thresholds, defibrillator 21 is instructed by apparatus 20 at 32 to issue a countershock. It is then determined at 34 whether the countershock resulted in conversion of the ventricular fibrillation to a pulsatile rhythm. If not, then the above-identified procedure is repeated. If conversion to a pulsatile rhythm is achieved, subject 22 is monitored and treated at 35 in order to maintain a pulsatile rhythm. If subject 22 is determined at any time not to have a pulsatile rhythm at 35, the ECG signal from subject 22 is again processed at 26.

If it is determined at 30 that both of the parameters $F_c$ and $F_p$ are below their respective thresholds, then a non-countershock therapy may be instituted at 36. In a preferred form, the alternative therapy is chosen as a function of the value of $F_c$ and/or $F_p$. Such alternative therapy may include utilizing drugs, manual cardiopulmonary resuscitation, mechanical resuscitation through the use of resuscitator 25, and/or ventilation/oxygenation.

The prescribed intervention is carried out at 38. The electrical potential generated by the subject's heart can be continuously sampled at 26 and processed to obtain the value of $F_c$ and/or $F_p$. The intervention protocol is either changed, modified, or kept the same at 36 and carried out at 38. In this manner, the therapy may be titrated to achieve the appropriate values of the parameters $F_c$ and/or $F_p$. When the predetermined threshold values of $F_c$ and/or $F_p$ are reached or exceeded at 30, as a result of titrating the therapy to the subject (26, 28, 30, 36, 38), a countershock may be administered at 32.

Thus, method 23 may be utilized to select the type and dosage of a drug. Method 23 may also be used to determine an optimum rate, force, and/or depth of compression of manual or mechanical CPR, or to select the compression-to-ventilation ratio of concurrent subject ventilation. Method 23 may be utilized for optimizing all forms of cardiopulmonary resuscitation, such as closed-chest CPR, open-chest cardiopulmonary resuscitation, and CPR which utilizes any mechanical adjunct. In this manner, method 23 may be utilized with mechanical resuscitators, ventricular assist devices, and cardiopulmonary bypass techniques performed during open-heart procedures. Thus, method 23 provides a feedback loop to monitor myocardial perfusion, titrate therapy, and optimize perfusion techniques during all forms of CPR.

Method 23 may also be utilized to select a defibrillation threshold, which is defined as the minimum amount of energy and/or current required to convert the cardiac rhythm from a ventricular fibrillation to a non-ventricular fibrillation rhythm. Thus, a determination of the minimum amount of energy or current a defibrillator needs to deliver could be derived as a function of the value of $F_c$ and/or $F_p$. This could help minimize myocardial injury and also save energy for the battery of defibrillators. Method 23 may also be used to estimate the optimum waveform and/or paddle position to use when delivering a countershock. Method 23 may be used to treat subjects experiencing involuntary cardiac arrest, but may also be used to restart a heart that has been intentionally placed into ventricular fibrillation for cardio-vascular surgery or the like. Although the heart is perfused during surgery, lactic acid and other products may accumulate in the myocardium. Method 23 provides a technique for ensuring optimum perfusion and that non-productive countershocks will not be administered.

Figure 3:
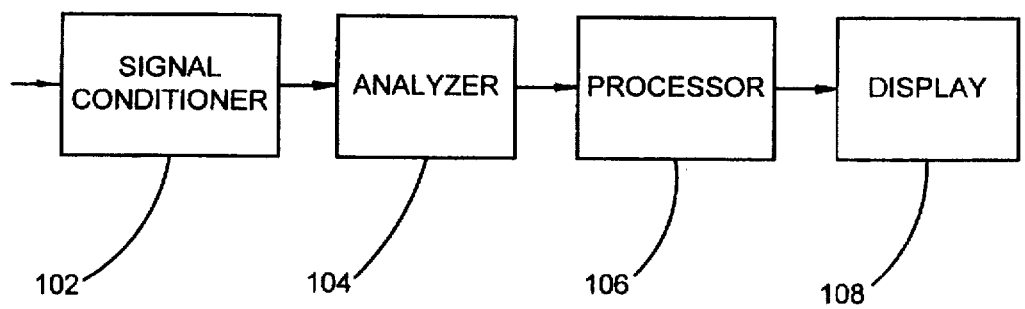
FIG. 3 is a block diagram of the apparatus in FIG. 1.

A subject monitor apparatus 100 includes an analyzer 104 for determining at least one amplitude parameter of the ECG time-domain signal interval or frequency parameter of a power spectrum following fast Fourier analysis of the subject's ECG (FIG. 3). Conditioning unit 102 amplifies, filters, and digitizes the subject's ECG. A processor 106 resolves the values of the parameter or parameters determined by analyzer 104 into clinically useful characteristics of the subject's heart, which may be displayed on display 108, along with the values of the parameters themselves, if desired. Signal conditioner 102 may be provided by an external apparatus, such as an ECG monitor or a defibrillator, or may be included with apparatus 100. Apparatus 100 may be useful for a research monitor to display the results of experimental interventions on animal or human subjects or as a subject monitor to read out vital characteristics of the heart of a subject in an emergency room, critical care unit, or the like.

Figure 4:
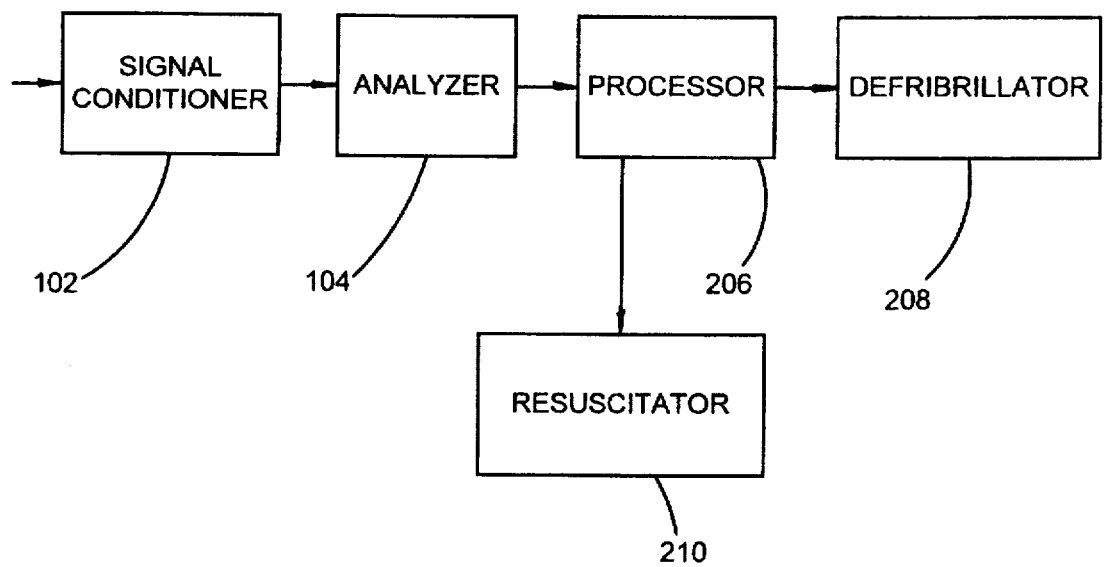
FIG. 4 is a block diagram of an alternative apparatus, according to the invention.

A treatment apparatus 200 is provided that includes a processor 206 that is capable of making a determination to administer an electrical countershock and to control a defibrillator 208 in applying the countershock to the subject (FIG. 4). This may include the timing, energy, current, waveform, or the like, of the countershock. Apparatus 200 may additionally include an output for controlling a resuscitator 210 or other mechanical-administering adjunct. Apparatus 200 may be built into defibrillator 208 in a compact housing along with a microcomputer to carry out the functions of conditioner 102, analyzer 104, and processor 206, or may be a separate unit. The above example is for illustration purposes only. It should be understood that apparatus 200 may include only a defibrillator, 208, only a resuscitator, 210, or both.

Other functions may be included with apparatus 100, 200. For example, an event marker may be included in order to allow a particular event to be time-stamped in the apparatus, such as a drug administration or the like.

Thus, it is seen that the present invention provides a method and an apparatus that may be incorporated into existing ECG monitors and/or defibrillators in order to provide manual, semi-automatic, or automatic subject treatment devices, as well as to be used as a stand-alone monitor. The invention may be applied to subjects of all species, habitus, underlying pathophysiology, and duration of ischemia. Because the invention includes a reliable procedure for determining the ability of the subject's heart to be converted to a pulsatile rhythm following countershock, damage to the myocardium resulting from cumulative energy from one, or a succession, of countershocks may be avoided. The present invention additionally provides the ability to regulate the level of therapeutic interventions and, thereby, avoid damage from unnecessary interventions or interventions greater than that required. The invention additionally provides the ability to accurately monitor myocardial perfusion and, thus, the metabolic state of the subject's heart based upon the recognition that $F_c$ is positively correlated with myocardial perfusion pressure during CPR. Since $F_c$ and $F_p$ are predictive of successful outcomes from countershock which is dependent upon myocardial perfusion, then $F_p$ should also be positively correlated with myocardial perfusion pressure during CPR. The parameters $F_c$ and $F_p$ in combination provide an especially reliable prediction of the ability of the subject's heart to be converted to a pulsatile rhythm following countershock.

EXAMPLE

A retrospective analysis of ECG cassette recordings obtained during cardiac arrest of 55 human subjects with out-of-hospital cardiac arrest whose initial ECG rhythms were identified as ventricular fibrillation. Subjects were monitored with a semi-automatic defibrillator/ECG monitor equipped with an ECG and voice cassette recording, such as MODEL HEART AID 1000 defibrillator/monitor, HEARTSTART 1000 defibrillator/monitor, HEARTSTART 2000 defibrillator/monitor marketed by Laerdal Corporation in Armonk, N.Y. The frequency bandwidth of the ECG recording was 1.7–20 Hz. The recorded ECG signals were digitized with an analog-to-digital converter, Model No. DT-2801A marketed by Data Translation, of Marlborough, Mass. The analog-to-digital conversion was done at 64 Hz and analyzed on an IBM compatible microcomputer utilizing a program written in ASYST commercial scientific software package language, Version 4.01, marketed by Keithley Instrument Company in Taunton, Mass. The ECG signals were processed in the same manner disclosed in U.S. Pat. No. 5,077,667 to Charles G. Brown and Roger Dzwonczyk. Each electrical countershock was identified on the ECG recording and a four-second epoch just prior to each countershock was analyzed. Each time-domain signal epoch was transformed into the frequency domain using a fast Fourier transform algorithm. Centroid frequency ($F_c$) and peak power frequency ($F_p$) were extracted from the resulting power spectrum. Average segment amplitude (SA) and average wave amplitude (WA) were extracted from the original time domain ECG epoch. The portion of the ventricular fibrillation ECG signal extending from peak to the following adjacent trough is defined as a "wave." Wave amplitude is the difference between the peak and trough amplitude of a wave. The average wave amplitude was obtained by calculating the average of all peak-to-trough wave amplitudes in the epoch. The average segment amplitude was obtained by calculating the average of the full-wave rectified signal epoch. To be included in the calculation of WA, the peak and trough must have been at least 0.256 seconds apart in time. The parameters WA and SA are reported in microvolts and provide an estimate of the average amplitude of a time-domain signal in the epoch.

The result of each countershock was also recorded and paired with the corresponding parameter values. A successful countershock was defined as the conversion of ventricular fibrillation to a supraventricular rhythm associated with a palpable pulse or blood pressure of any duration within two minutes of the countershock without ongoing CPR. Emergency Medical Services'(EMS) records were reviewed retrospectively to determine the result of each countershock. A countershock was eliminated from analysis if the ECG signal prior to the countershock contained identifiable artifact, such as interference from cardiopulmonary resuscitation, or other noise. The subjects received a total of 324 countershocks. However, only 128 of the countershocks were free of artifact. Nine of the 128 countershocks considered were successful, namely they resulted in conversion to a pulsatile rhythm. Each countershock was analyzed as an independent event. The mean range, and median values for each parameter were determined for unsuccessful and successful countershocks. A Kolmogorov-Smirnov comparison was performed on the parameters $F_c$, $F_p$, SA, and WA in relation to countershock success, return of spontaneous circulation ever, survival to admission to hospital, and survival to discharge from hospital.

Figure 5:
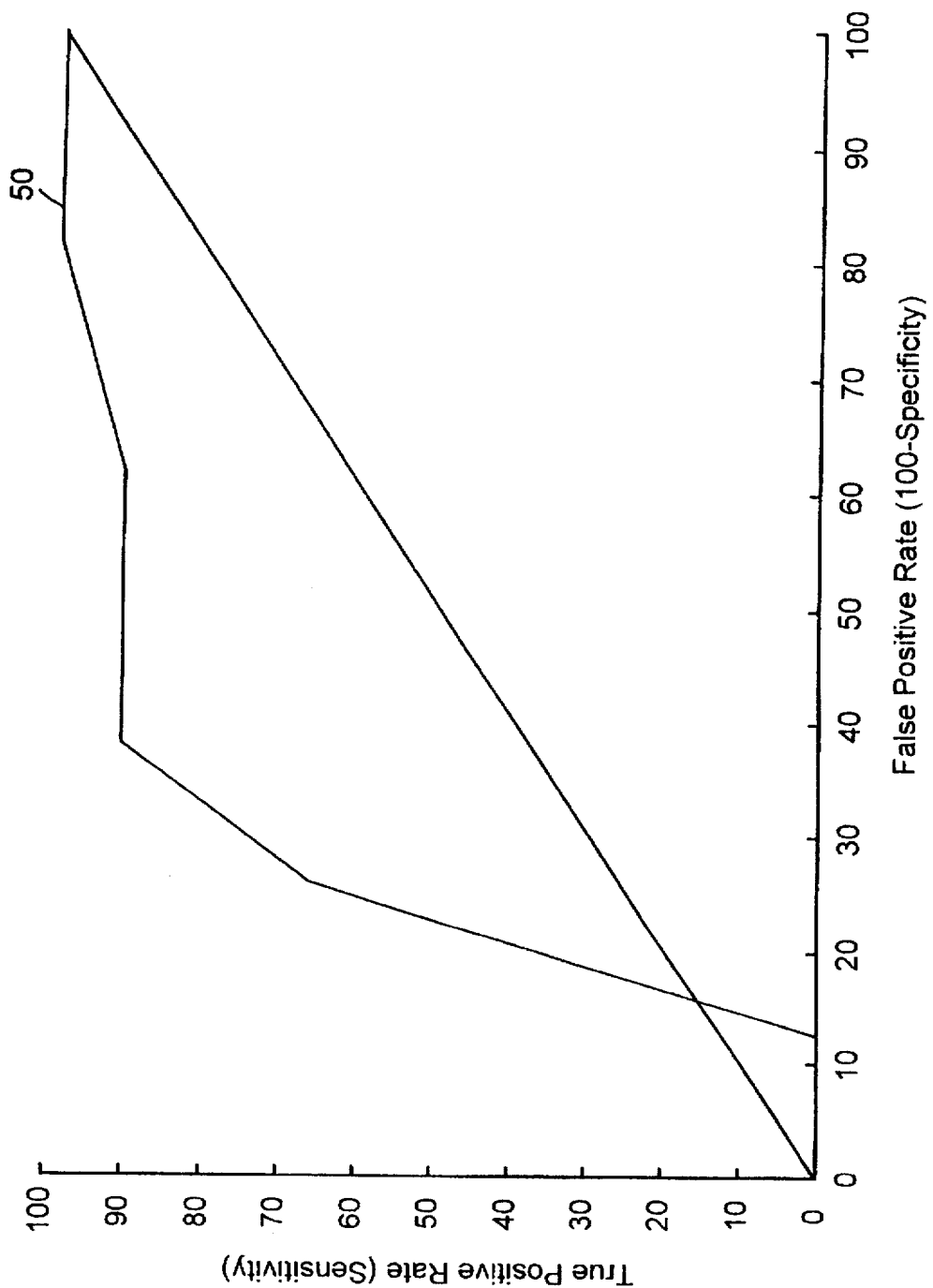
FIG. 5 is a graph illustrating a receiver operating characteristic curve of the centroid frequency of the power spectrum for an outcome of successful countershock.
Figure 6:
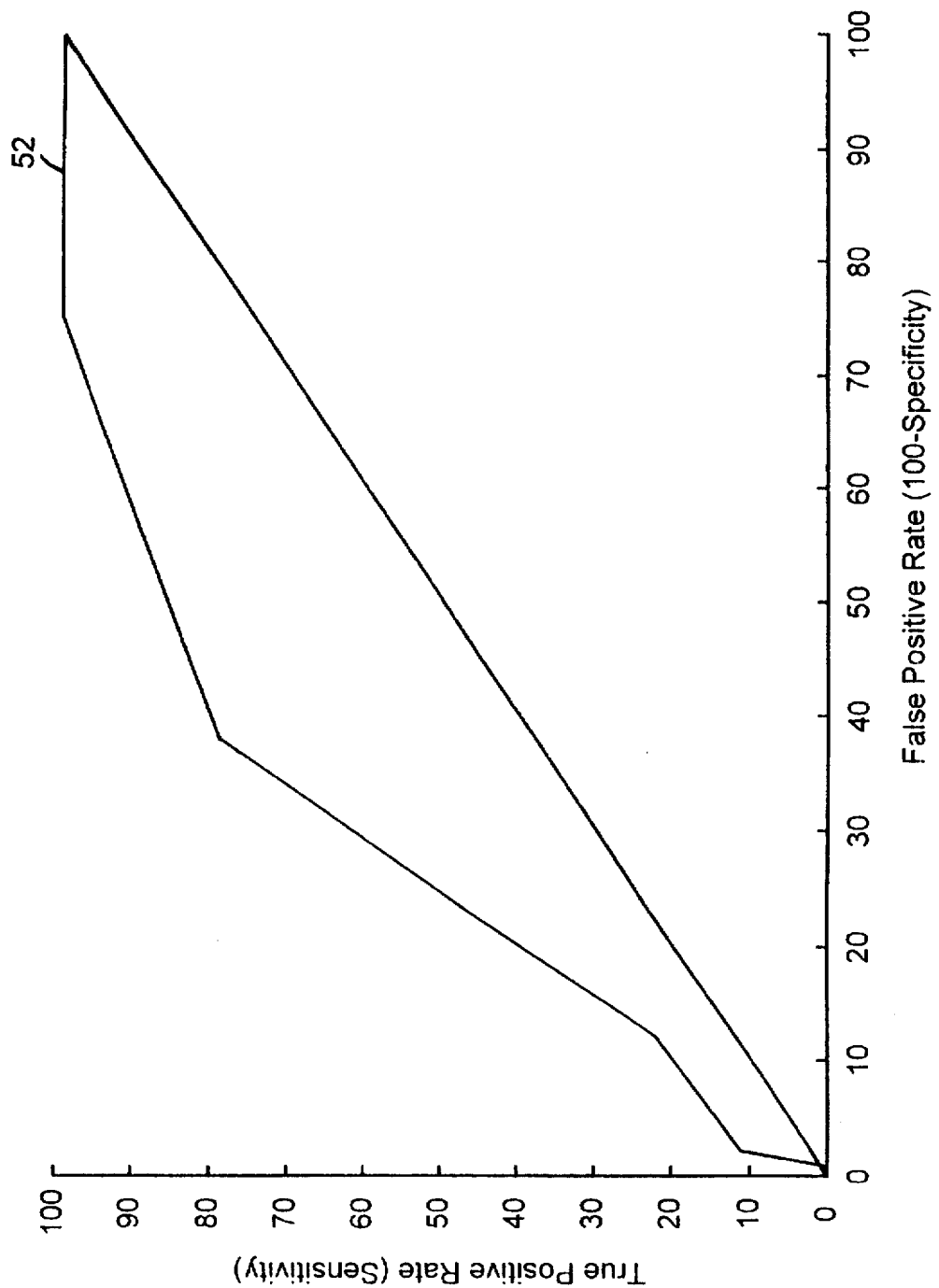
FIG. 6 is a graph illustrating a receiver operating characteristic curve of the peak power frequency of the power spectrum for an outcome of successful countershock.
Figure 7:
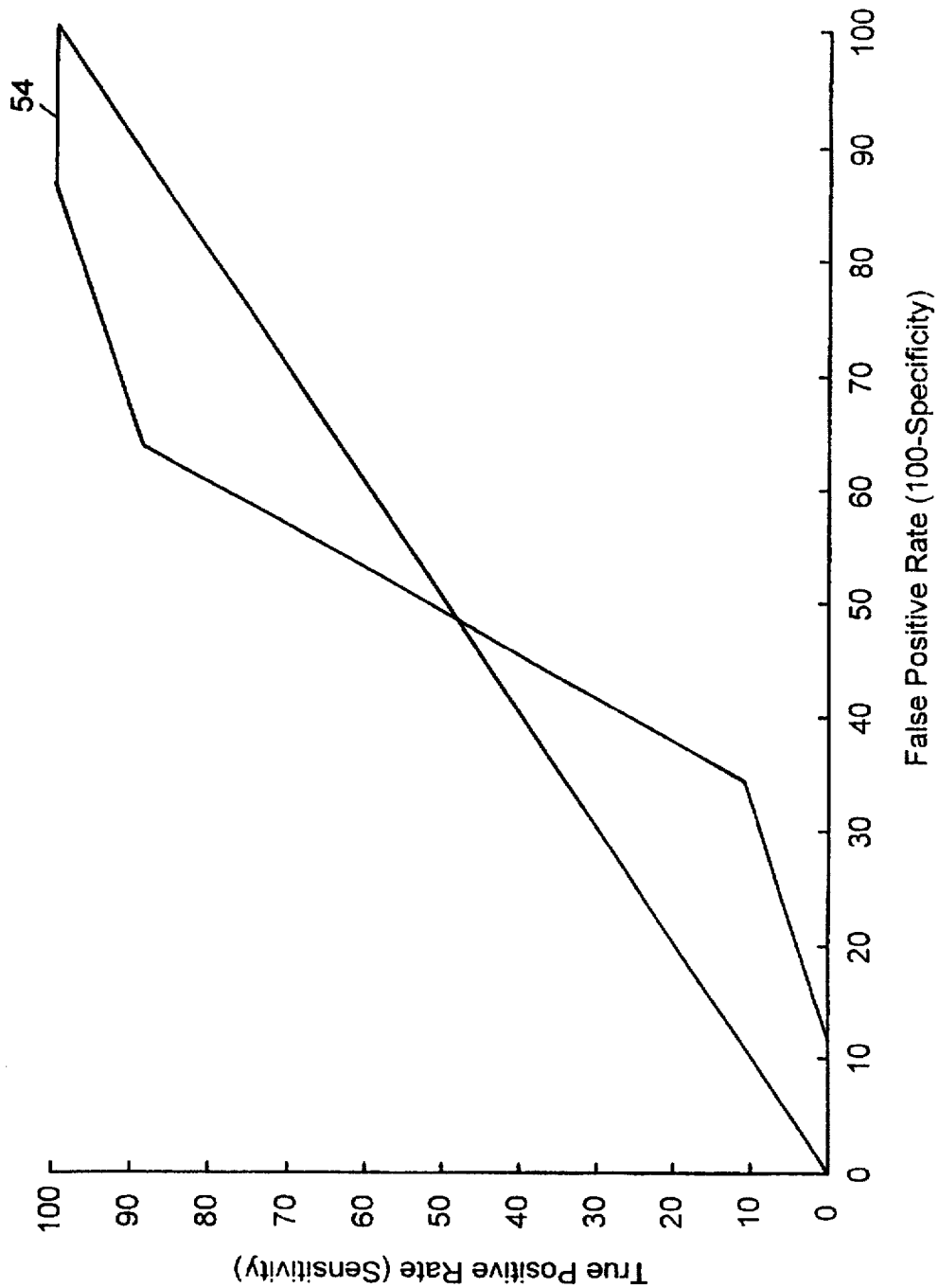
FIG. 7 is a graph illustrating a receiver operating characteristic curve of the average segment amplitude of the power spectrum for an outcome of successful countershock.
Figure 8:
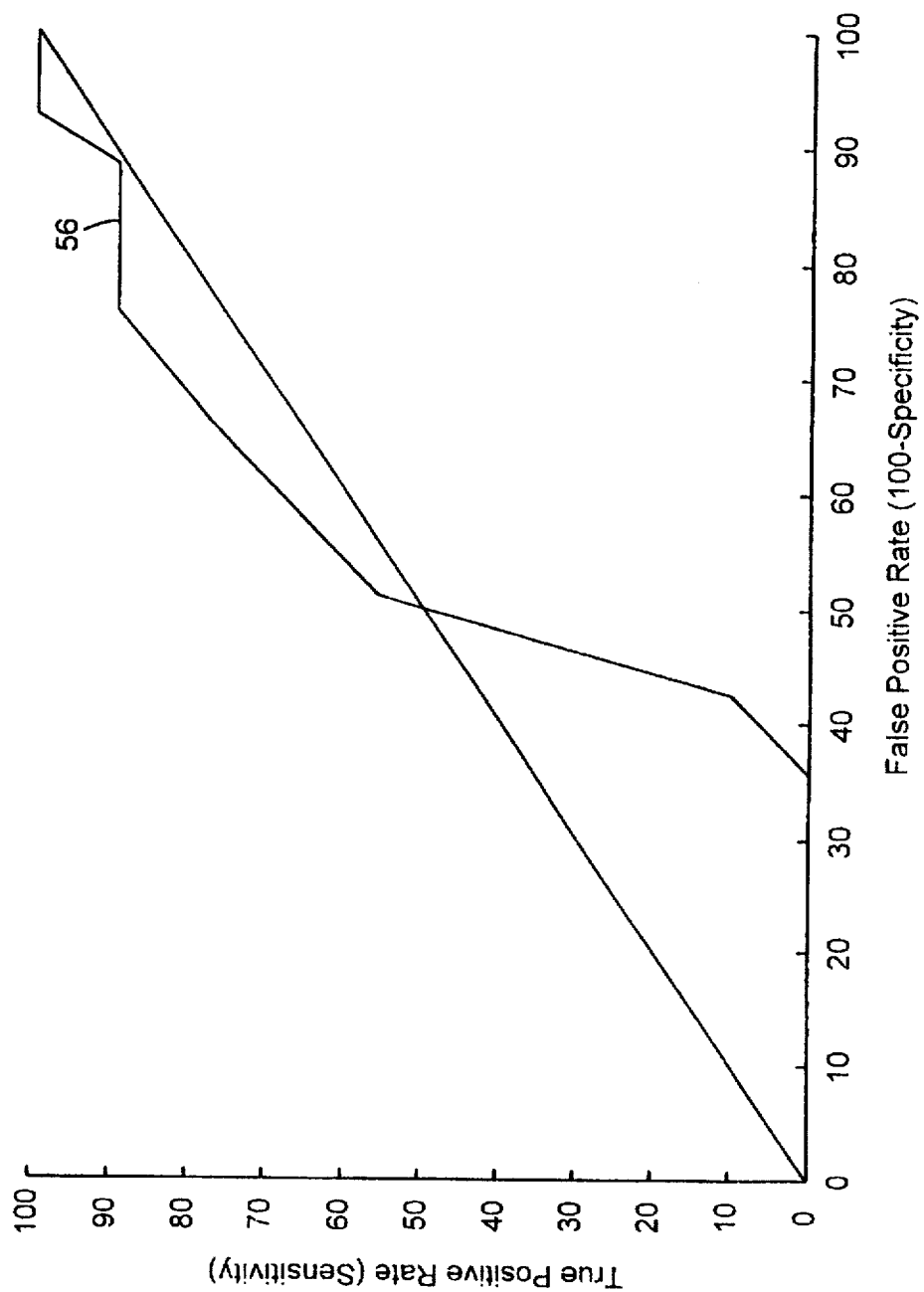
FIG. 8 is a graph illustrating a receiver operating characteristic curve of the average wave amplitude of the power spectrum for an outcome of successful countershock.

The value for determining 100% sensitivity and maximum specificity of each parameter alone, and in combination, was determined. The term "sensitivity" of the parameter is the probability that the parameter will be equal to or greater than a specific value given that the subject is successfully countershocked. The "specificity" of the parameter is the probability that the parameter will be less than a specific value given that the subject is not successfully countershocked. The value of each parameter as a predictor of clinically relevant cardiac arrest outcomes was determined by calculating the area under the receiver operating characteristic (ROC) curve. An ROC curve 50 of the parameter $F_c$ for an outcome of successful countershock is illustrated in FIG. 5. The area under ROC curve 50 represents the probability to which $F_c$ can be used to predict successful countershock. The area under curve 50 is 0.717. An ROC curve 52 of the parameter $F_p$ for an outcome of successful countershock is illustrated in FIG. 6. The area under ROC curve 52 represents the probability to which $F_p$ can be used to predict success. The area under curve 52 is 0.697. A review of FIGS. 5 and 6 illustrates the significant ability of the parameters to predict successful countershock of the subject. The significant area under ROC curves 50 and 52 is in contrast to ROC curve 54 of the parameter SA, for an outcome of successful countershock (FIG. 7), and ROC curve 56 of the parameter WA (FIG. 8) for an outcome of successful countershock. Curves 54 and 56 have significant negative as well as positive areas, which indicates the inability of the parameters SA and WA to predict successful countershock of the subject.

A statistical analysis for the parameters $F_c$, $F_p$, SA, and WA for a cardiac arrest outcome of successful countershock, which is defined for the purpose of this analysis to be the return of spontaneous circulation within two (2) minutes of the countershock, is shown in Table 1:

TABLE 1

| | COUNTERSHOCK OUTCOME | | | | | | |
|---|---|---|---|---|---|---|---|
| | SUCCESSFUL | | | UNSUCCESSFUL | | | P-Value |
| Parameter | Mean | Range | Median | Mean | Range | Median | |
| $F_c$ | 5.48 ± 0.67 | 3.86–6.12 | 5.66 | 4.85 ± 1.16 | 2.62–9.75 | 4.67 | 0.012 |
| $F_p$ | 5.31 ± 1.24 | 3.50–7.75 | 5.00 | 4.29 ± 1.63 | 0.25–11.0 | 4.00 | 0.066 |
| SA | 133 ± 32 | 70–180 | 142 | 132 ± 61 | 20–260 | 129 | 0.549 |
| WA | 386 ± 95 | 190–530 | 412 | 384 ± 184 | 50–800 | 366 | 0.337 |

It can be seen from Table 1 that the mean value of $F_c$ was significantly higher for successful countershock than for unsuccessful countershock, with P=0.012. The statistical difference for $F_p$ (P =0.066), SA (P=0.549), and WA (P=0.337) falls outside of the statistical significance of the test of P≦0.05. Further analysis also illustrates that, when the parameters $F_p$ and $F_c$ are used in combination and when the value of $F_p$ falls within the range of 3.5 Hz to 7.75 Hz and the parameter $F_c$ falls within the range of 3.86 Hz to 6.12 Hz, the combination has a sensitivity of 100% and a specificity of 47.1% in predicting successful countershock.

Table 2 illustrates a statistical analysis for the parameters $F_c$ and $F_p$ with a successful outcome defined as a return of spontaneous circulation more than two minutes after countershock:

TABLE 2

RETURN OF SPONTANEOUS CIRCULATION EVER

| | SUCCESSFUL | | | UNSUCCESSFUL | | | P-Value |
|---|---|---|---|---|---|---|---|
| Parameter | Mean | Range | Median | Mean | Range | Median | |
| $F_c$ | 5.02 ± 1.10 | 2.62–8.75 | 4.97 | 3.96 ± 1.22 | 2.68–5.58 | 3.45 | 0.101 |
| $F_p$ | 4.63 ± 1.67 | 0.25–11.00 | 4.75 | 2.50 ± 0.57 | 1.75–3.00 | 2.75 | 0.003 |

It can be seen from Table 2 that the mean value of $F_p$ was significantly higher for successful return of spontaneous circulation ever than for unsuccessful return of spontaneous circulation ever, with P=0.003. The statistical difference for $F_c$(P=0.101) falls outside of the statistical significance of the test.

Table 3 illustrates a statistical analysis for the parameters $F_c$ and $F_p$ with a successful outcome defined as a survival to admission to a hospital:

TABLE 3

SURVIVAL TO ADMISSION TO HOSPITAL

| | SUCCESSFUL | | | UNSUCCESSFUL | | | P-Value |
|---|---|---|---|---|---|---|---|
| Parameter | Mean | Range | Median | Mean | Range | Median | |
| $F_c$ | 5.22 ± 1.22 | 2.62–8.75 | 5.37 | 4.52 ± 0.92 | 2.68–6.91 | 4.51 | 0.001 |
| $F_p$ | 4.82 ± 1.89 | 0.25–11.00 | 4.75 | 3.83 ± 1.21 | 1.75–7.00 | 3.75 | 0.001 |

It can be seen from Table 3 that the mean values of both $F_c$ and $F_p$ were significantly higher for successful survival to admission to hospital than for unsuccessful, with P=0.001 for each.

Table 4 illustrates a statistical analysis for the parameters $F_c$ and $F_p$ with a successful outcome defined as a survival to discharge from a hospital:

TABLE 4

SURVIVAL TO DISCHARGE FROM HOSPITAL

| | SUCCESSFUL | | | UNSUCCESSFUL | | | P-Value |
|---|---|---|---|---|---|---|---|
| Parameter | Mean | Range | Median | Mean | Range | Median | |
| $F_c$ | 6.17 ± 0.38 | 5.63–6.73 | 6.10 | 4.64 ± 1.03 | 2.62–6.91 | 4.63 | 0.0001 |
| $F_p$ | 6.00 ± 1.15 | 4.00–7.75 | 5.88 | 4.05 ± 1.38 | 1.75–7.75 | 3.75 | 0.002 |

It can be seen from Table 4 that the mean value of both $F_c$ and $F_p$ were significantly higher for successful discharge from the hospital than for unsuccessful, with P=0.0001 and 0.002, respectively.

Figure 9:
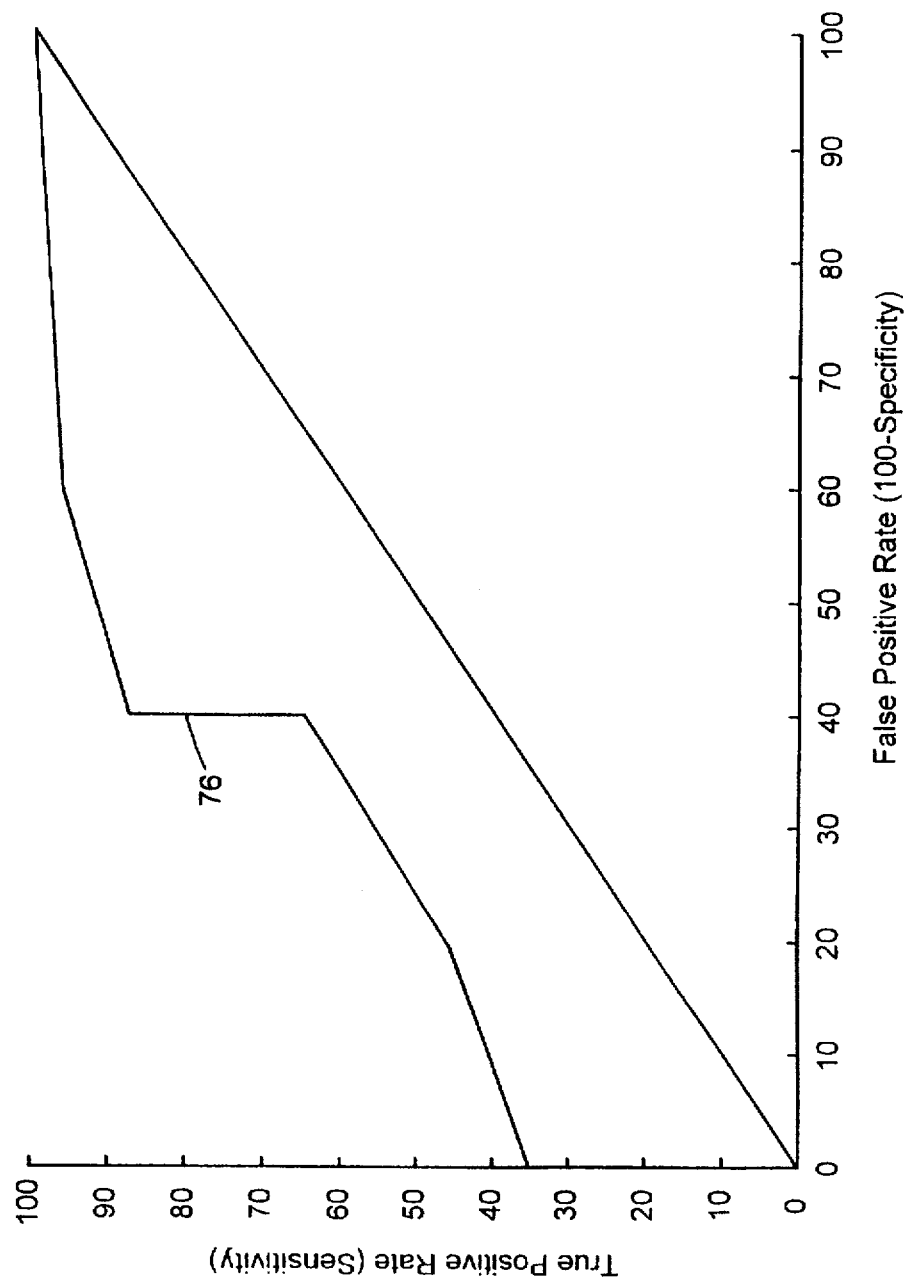
FIG. 9 is a graph illustrating a receiver operating characteristic curve of the centroid frequency of the power spectrum for an outcome of return of spontaneous circulation ever.
Figure 10:
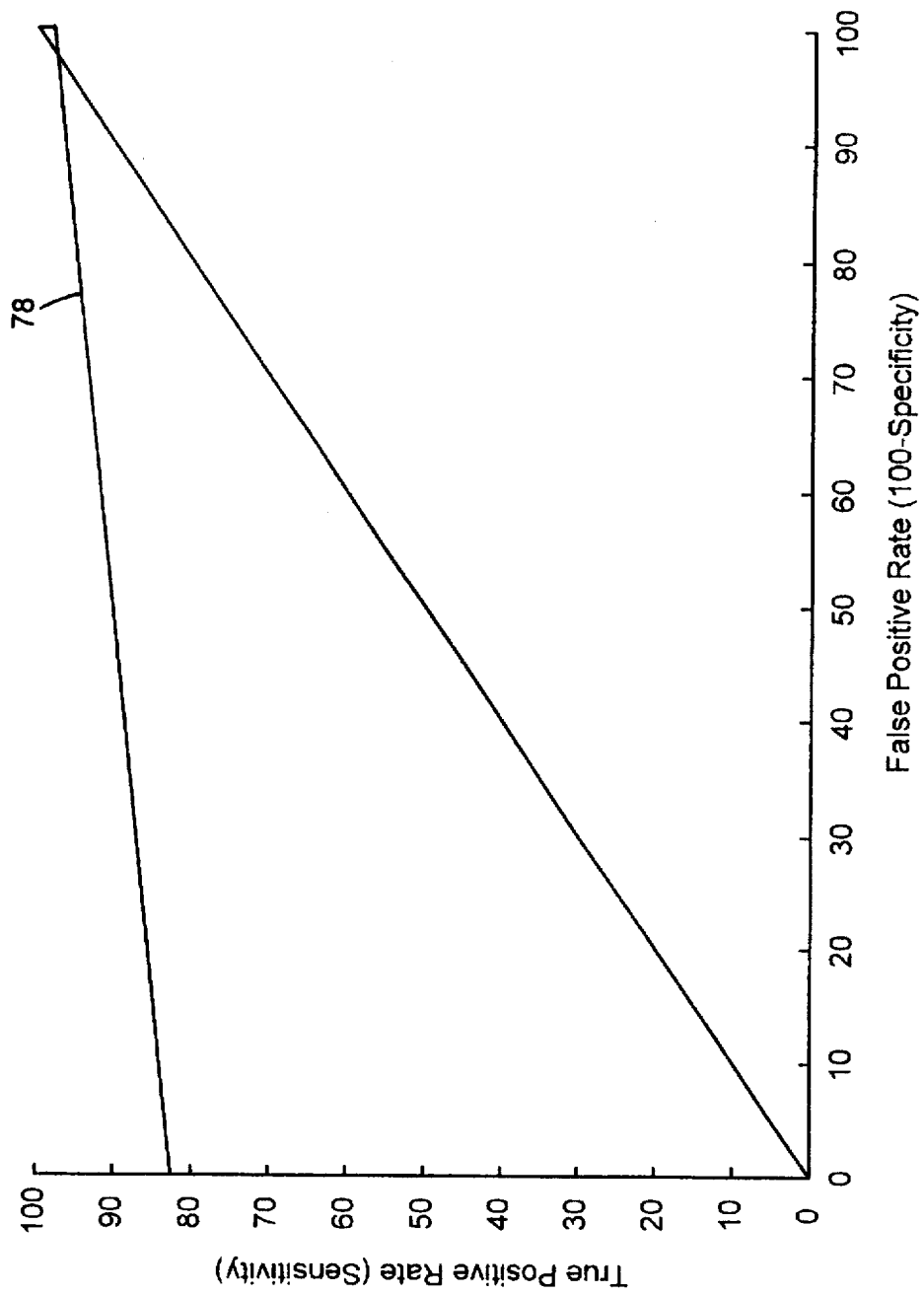
FIG. 10 is a graph illustrating a receiver operating characteristic curve of the peak power frequency of the power spectrum for an outcome of return of spontaneous circulation ever.
Figure 11:
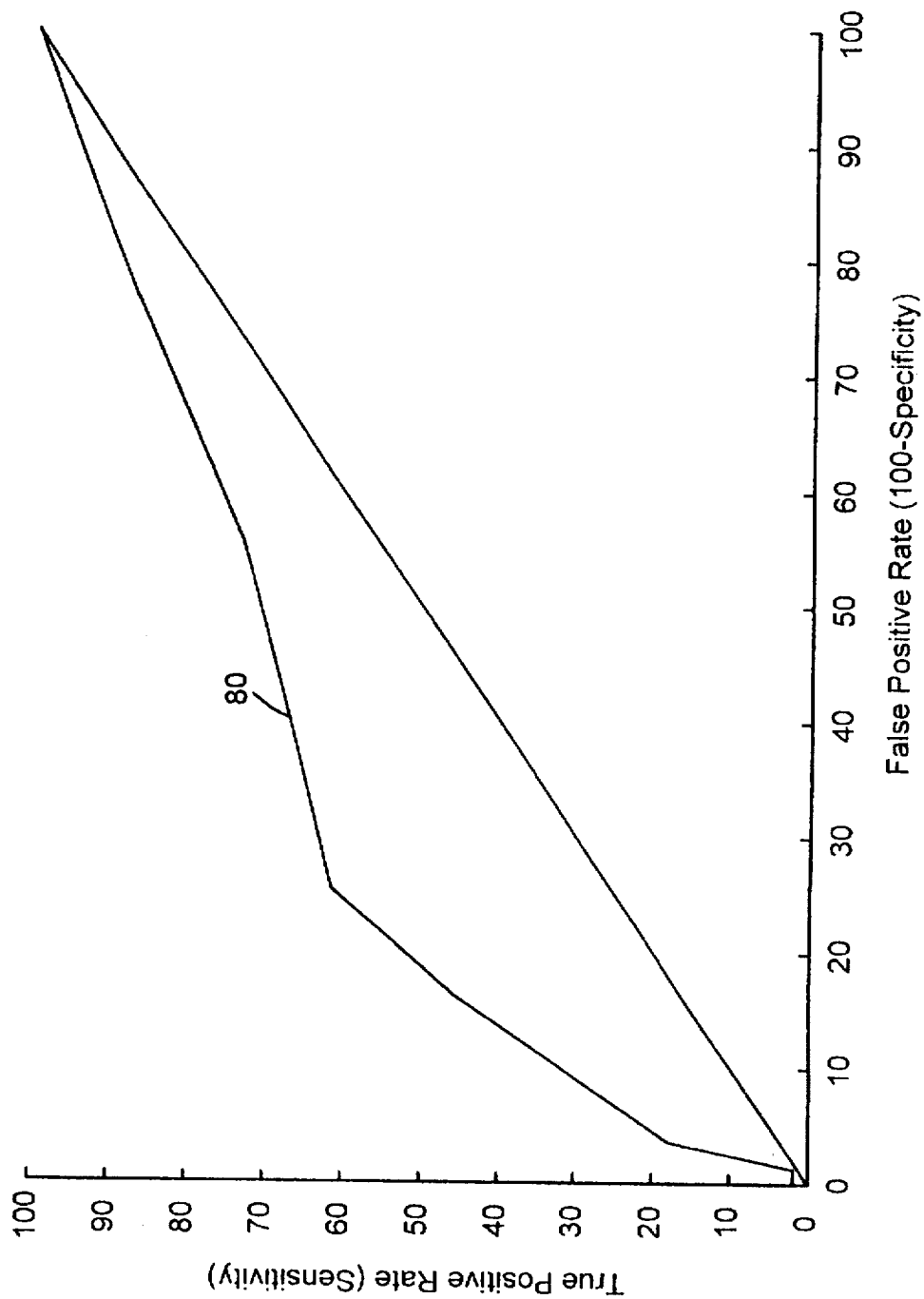
FIG. 11 is a graph illustrating a receiver operating characteristic curve of the centroid frequency of the power spectrum for an outcome of survival to hospital admission.
Figure 12:
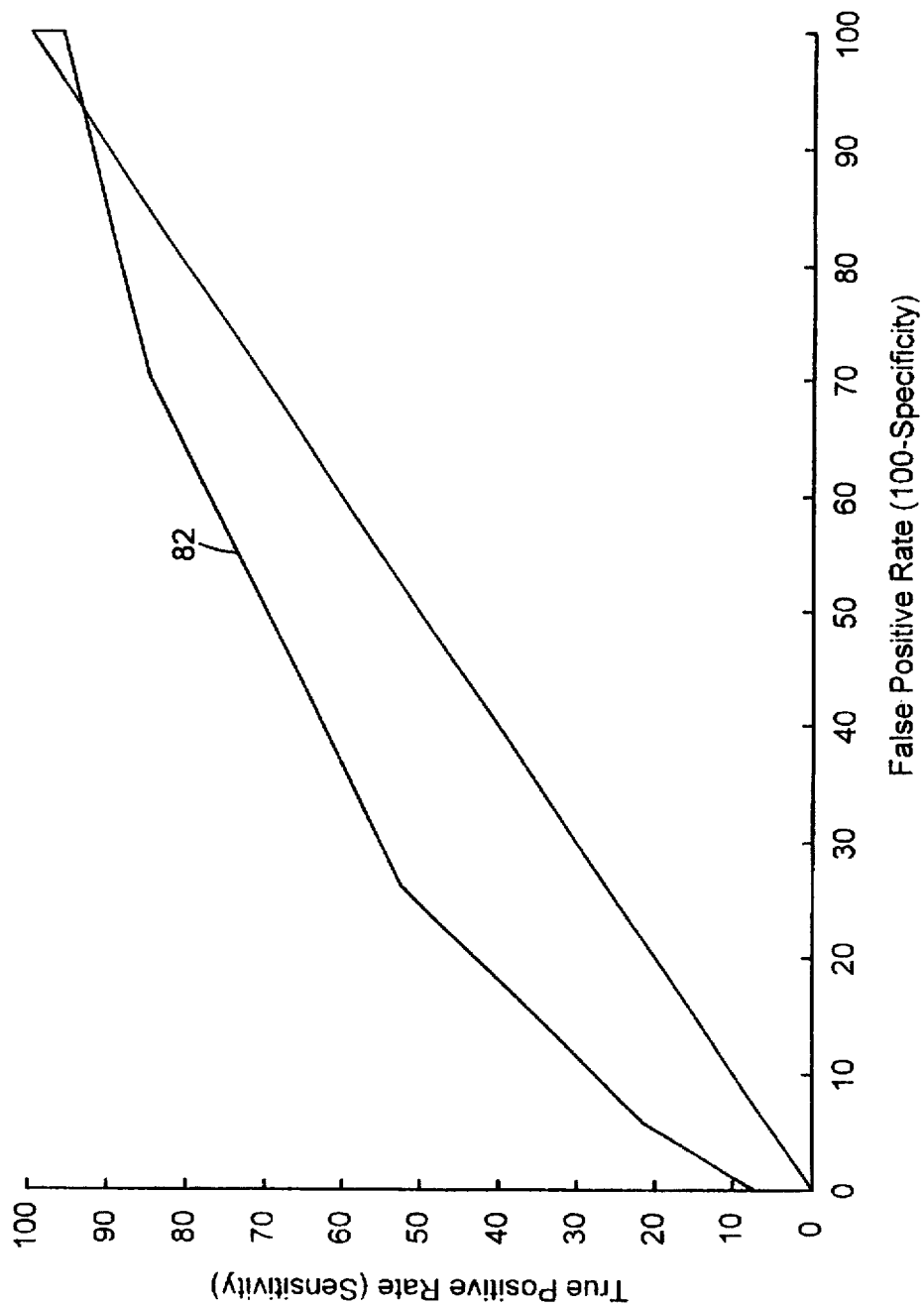
FIG. 12 is a graph illustrating a receiver operating characteristic curve of the peak power frequency of the power spectrum for an outcome of survival to hospital admission.
Figure 13:
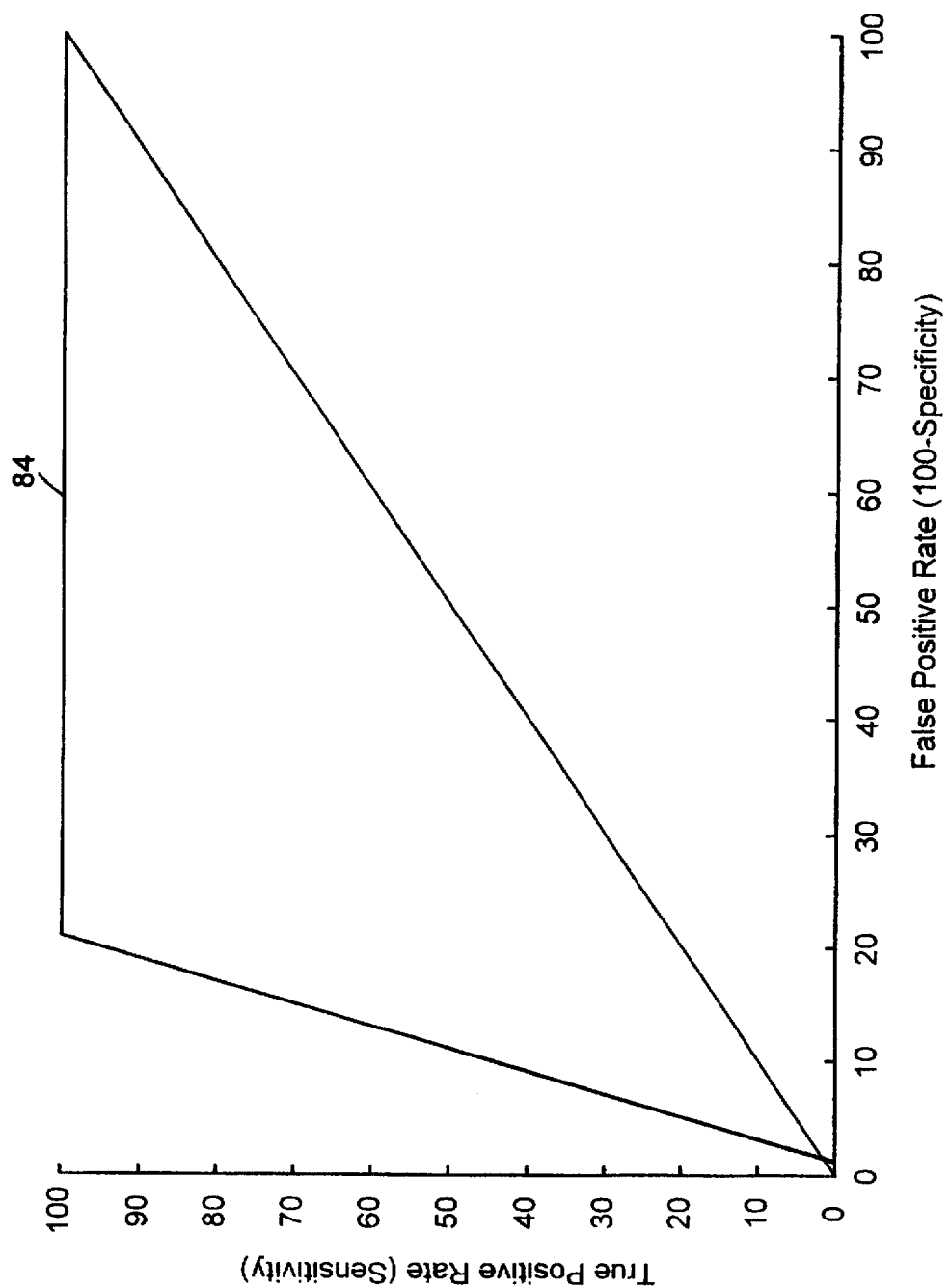
FIG. 13 is a graph illustrating a receiver operating characteristic curve of the centroid frequency of the power spectrum for an outcome of survival to hospital discharge.
Figure 14:
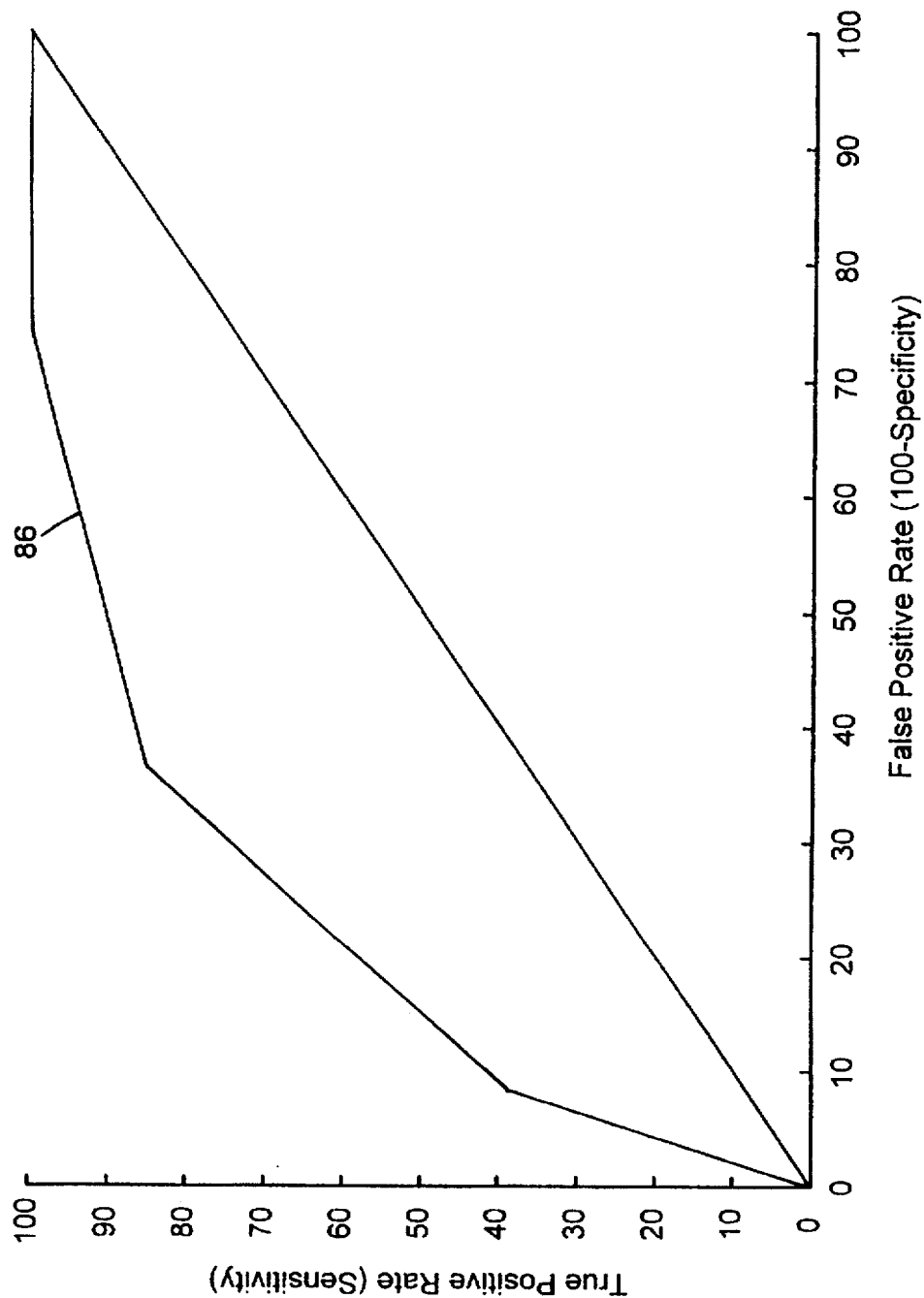
FIG. 14 is a graph illustrating a receiver operating characteristic curve of the peak power frequency of the power spectrum for an outcome of survival to hospital discharge.

An ROC curve 76 of $F_c$ for the outcome of whether the subject ever experienced a return of spontaneous circulation, is illustrated in FIG. 9. The area under curve 76 is 0.767. An ROC curve 78 of the parameter $F_p$, for the outcome of whether the subject ever experienced a return of spontaneous circulation, is illustrated in FIG. 10. The area under curve 78 is 0.890. An examination of the areas under curves 76 and 78 illustrates the significant predictive value of these parameters for return of spontaneous circulation ever. An ROC curve 80 of the parameter $F_c$ for the successful outcome of survival to admission to a hospital is illustrated in FIG. 11. The area under curve 80 is 0.656. Likewise, the ROC curve 82 of the parameter $F_p$ for the successful outcome of survival to admission to a hospital is illustrated in FIG. 12. The area under curve 82 is 0.616. An ROC curve 84 of the parameter $F_c$ for the successful outcome of survival to discharge from a hospital is illustrated in FIG. 13 and an ROC curve 86 of the parameter $F_p$ for survival to discharge is illustrated in FIG. 14. The area under curve 84 is 0.886 and the area under curve 86 is 0.835. A review of the areas under curves 80, 82, 84, and 86 illustrates the predictive value of these parameters.

Thus, it is seen that the present invention provides a useful method and apparatus for both guiding interventions for subjects experiencing cardiac arrest as well as predicting the likelihood that particular interventions will be successful. Although the invention has application in treating human subjects in cardiac arrest, it may also be used as a research monitor for evaluating the effect of interventions on human subjects, or used on other animal subjects, in which cardiac arrest is induced. Changes and modifications in the specifically described embodiments can be carried out without departing from the principles of the invention, which is intended to be limited only by the scope of the appended claims, as interpreted according to the principles of patent law including the doctrine of equivalents.

The embodiments of the invention in which an exclusive property or privilege is claimed are defined as follows:

1. An apparatus that non-intrusively provide a clinically useful indicator of the condition of the heart of a subject in ventricular fibrillation or asystole from an electrocardiogram of the heart, said electrocardiogram made up of time domain sample of electrical signals, comprising:

an analyzer for transforming said domain samples of an electrocardiogram of a heart in one of ventricular fibrillation and asystole to a frequency domain power spectrum and for determining at least one parameter of said power spectrum that is predictive of a clinically relevant cardiac arrest outcome for the subject, said outcome being the subject surviving until an occurrence of at least one particular future event; and a processor that resolves said at least one parameter to a clinically useful characteristic of the subject's heart.

2. The apparatus in claim 1 wherein said processor resolves at least one of a centroid frequency of said power spectrum and a peak power frequency of said power spectrum to said clinically useful characteristic.

3. The apparatus in claim 2 wherein said processor determines whether said at least one of a centroid frequency and a peak power frequency is equal to or above a predetermined threshold.

4. The apparatus in claim 1 wherein said clinically useful characteristic of the subject's heart is the metabolic state of the myocardium.

5. The apparatus in claim 1 wherein said at least one parameter includes at least two said parameters.

6. The apparatus in claim 5 wherein said at least two parameters includes the centroid frequency and peak power frequency of the power spectrum.

7. The apparatus in claim 1 including a display for displaying at least one of said at least one parameter and said clinically useful characteristic.

8. The apparatus in claim 1 including an event marker for receiving user input designations of the occurrence of events.

9. The apparatus in claim 1 wherein said at least one particular future event is selected from a group consisting of eventual return of spontaneous circulation of the subject, admission of the subject to a medical care facility and discharge of the subject from a medical care facility.

10. An apparatus for guiding the administration of therapy to a subject in ventricular fibrillation or asystole from an electrocardiogram of the heart made up of time domain samples of analog electrical potential, comprising:

an analyzer for transforming said time domain samples of an electrocardiogram of a heart in one of ventricular fibrillation and asystole to a frequency domain power spectrum and for determining a value that is predictive of the subject surviving until occurrence of at least one particular future event based on said frequency domain power spectrum;

a processor coupled to said analyzer; and at least one therapy-administering device coupled to and controlled by said processor for administering therapy to the subject;

wherein said processor is adapted to controlling said therapy-administering device as a function of said value.

11. The apparatus in claim 10 wherein said therapy-administering device is a drug infusion device.

12. The apparatus in claim 11 wherein said processor selects a type and dosage of a drug to be administered by said drug infusion device as a function of said value.

13. The apparatus in claim 10 wherein said therapy-administering device is a defibrillator for administering a countershock.

14. The apparatus in claim 13 wherein said processor selects an electrical characteristic of a countershock to be administered by said defibrillator as a function of said value.

15. The apparatus in claim 14 wherein said electrical characteristic includes at least one of electrical energy and current.

16. The apparatus in claim 13 wherein said processor selects at least one of an electrical waveform to be administered by said defibrillator and a paddle position for said defibrillator as a function of said value.

17. The apparatus in claim 10 wherein said therapy-administering device is a cardiopulmonary resuscitator.

18. The apparatus in claim 17 wherein said processor selects at least one of a rate of compression, a depth of compression and a force of compression for said cardiopulmonary resuscitator as a function of said value.

19. The apparatus in claim 17 wherein said therapy administering device further includes a ventilator and wherein said processor selects a compression-to-ventilation ratio between said resuscitator and said ventilator as a function of said value.

20. The apparatus in claim 10 wherein said at least one particular future event is selected from a group consisting of eventual return of spontaneous circulation of the subject, admission of the subject to a medical care facility and discharge of the subject from a medical care facility.

21. An apparatus for guiding the administration of therapy to a subject in ventricular fibrillation or asystole from an electrocardiogram of the heart made up of time domain samples of analog electrical potential, comprising:

an analyzer for transforming said time domain samples of an electrocardiogram of a heart in one of ventricular fibrillation and asystole to a frequency domain power spectrum and for determining at least two frequency parameters that are predictive of a clinically relevant cardiac arrest outcome for the subject based upon said frequency domain power spectrum;

a processor coupled to said analyzer; and at least one therapy-administering device coupled to and controlled by said processor for administering therapy to the subject;

wherein said processor is adapted to controlling said therapy-administering device as a function of said at least two frequency parameters.

22. The apparatus in claim 21 wherein said therapy-administering device is a drug infusion device.

23. The apparatus in claim 22 wherein said processor selects a type and dosage of a drug to be administered by said drug infusion device as a function of said at least two frequency parameters.

24. The apparatus in claim 21 wherein said therapy-administering device is a defibrillator for administering a countershock.

25. The apparatus in claim 24 wherein said processor selects an electrical characteristic of a countershock to be administered by said defibrillator as a function of said at least two frequency parameters.

26. The apparatus in claim 25 wherein said electrical characteristic includes at least one of electrical energy and current.

27. The apparatus in claim 24 wherein said processor selects at least one of an electrical waveform to be administered by said defibrillator and a paddle position for said defibrillator as a function of said at least two frequency parameters.

28. The apparatus in claim 21 wherein said therapy-administering device is a cardiopulmonary resuscitator.

29. The apparatus in claim 28 wherein said processor selects at least one of a rate of compression, a depth of compression and a force of compression for said cardiopulmonary resuscitator as a function of said at least two frequency parameters.

30. The apparatus in claim 28 wherein said therapy administering device further includes a ventilator and wherein said processor selects a compression-to-ventilation ratio between said resuscitator and said ventilator as a function of said parameters.

31. The apparatus in claim 21 wherein said at least two frequency parameters are predictive of the subject surviving until the occurrence of at least one of eventual return of spontaneous circulation, admission of the subject to a medical care facility and discharge of the subject from a medical care facility.

32. The apparatus in claim 21 wherein said at least two frequency parameters include peak power frequency of said power spectrum and centroid frequency of said power spectrum.

* * * * *

UNITED STATES PATENT AND TRADEMARK OFFICE
CERTIFICATE OF CORRECTION

PATENT NO. : 5,683,424
DATED : November 4, 1997
INVENTOR(S) : Charles G. Brown and Roger R. Dzwonczyk It is certified that error appears in the above-identified patent and that said Letters Patent is hereby corrected as shown below:

Column 6, line 54:
    After "defibrillator/monitor," insert --or--.

Columns 7 and 8, TABLE 1, $F_c$/Range:
    "2.62-9.75" should be --2.62-8.75--.

Column 11, claim 1, line 6:
    "provide" should be --provides--.

Column 11, claim 1, line 10:
    "sample" should be --samples--.

Column 11, claim 1, line 11:
    After "said" insert --time--.

Signed and Sealed this

Fourth Day of July, 2000

Attest:

Q. TODD DICKINSON

Attesting Officer

Director of Patents and Trademarks